(12) United States Patent
Arvidsson et al.

(10) Patent No.: US 6,322,682 B1
(45) Date of Patent: Nov. 27, 2001

(54) METHOD FOR THE CAPILLARY ELECTROPHORESIS OF NUCLEIC ACIDS, PROTEINS AND LOW MOLECULAR CHARGED COMPOUNDS

(75) Inventors: Lars-Erik Arvidsson, Bjärred; Björn Ekström, Uppsala, both of (SE)

(73) Assignee: Gyros AB, Uppsala (SE)

( * ) Notice: Subject to any disclaimer, the term of this patent is extended or adjusted under 35 U.S.C. 154(b) by 0 days.

(21) Appl. No.: 09/214,020

(22) PCT Filed: Jul. 1, 1997

(86) PCT No.: PCT/SE97/01187

§ 371 Date: Sep. 23, 1999

§ 102(e) Date: Sep. 23, 1999

(87) PCT Pub. No.: WO98/00709

PCT Pub. Date: Jan. 8, 1998

(30) Foreign Application Priority Data

Jul. 3, 1996 (SE) .................................................. 9602638

(51) Int. Cl.[7] .......................... G01N 27/26; G01N 27/447

(52) U.S. Cl. .......................... 204/454; 204/451; 204/601
(58) Field of Search ...................... 204/454, 450, 204/451, 452, 455, 601, 602, 603, 604, 605

(56) References Cited

U.S. PATENT DOCUMENTS

| 3,728,145 | * | 4/1973 | Hjerten | 204/600 |
| 4,690,749 | * | 9/1987 | Van Alstine et al. | 204/454 |
| 5,015,350 | * | 5/1991 | Wikterowicz | 204/454 |

* cited by examiner

*Primary Examiner*—Jill Warden
*Assistant Examiner*—John S. Starsiak, Jr.
(74) *Attorney, Agent, or Firm*—Fulbright & Jaworski L.L.P.

(57) ABSTRACT

A method of capillary electrophoresis utilizing a capillary tube made up of hydrophobic plastics, charactarized in that the inner surface of said capillary is coated with a hydrophilic polymer comprising a polyhydroxy polymer exhibiting groups —B—R, where R is a hydrocarbyl group and B is a bridge binding to the polyhydroxy polymer, preferably by substituting a hydrogen in a hydroxy group of the polyhydroxy polymer.

11 Claims, 4 Drawing Sheets

Figure 1:
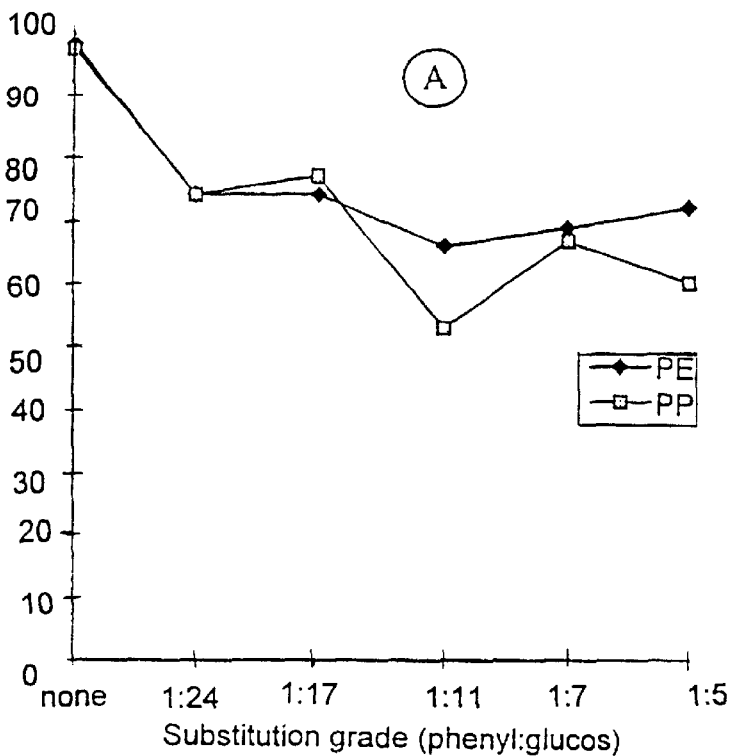
Figure 1:
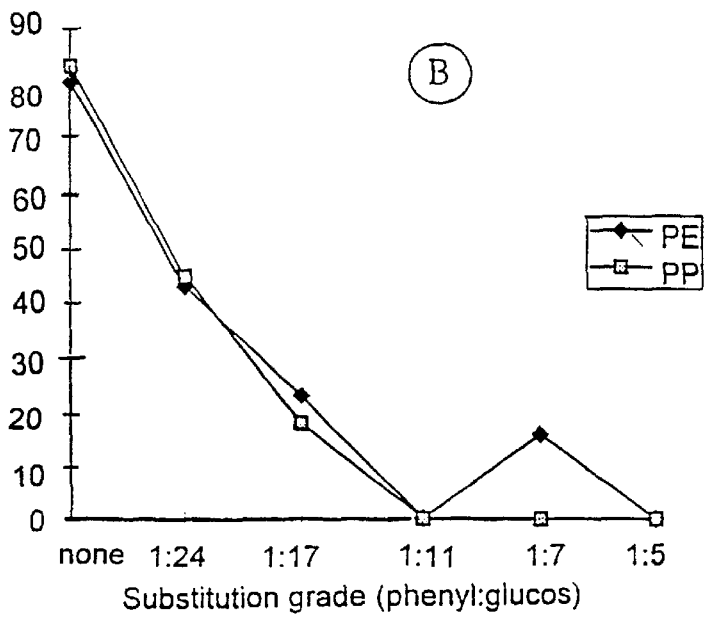

METHOD FOR THE CAPILLARY ELECTROPHORESIS OF NUCLEIC ACIDS, PROTEINS AND LOW MOLECULAR CHARGED COMPOUNDS

Hydrophobic polymeric materials are commonly utilized in laboratory equipment, medical supplies, membranes and have also recently found interest as column material in capillary electrophoresis (CE)(Liu et al., J. Microcol. Sep. 15 (1993) 245-). Unlike fused silica, these materials do not change surface characteristics depending on pH. Unfortunately it is difficult to fabricate hydrophilic materials with the same good mechanical properties as hydrophobic material.

Perfluorinated poly(ethylene-propylene) tubings (a flat 0.2×0.8 mm i.d. and a round 0.5 i.d.) have previously been evaluated as electrophoresis support by comparing IgG separation patterns (Izumi et al., J. High Resolut. 14 (1991) 351-). A higher voltage could be applied to the flat tubing owing to its smaller cross sectional area. The migration time in the analysis with the flat tubing was approximately 8 minutes shorter but without loss in resolution. The electrokinetic property of polymers of fluorinated hydrocarbons (PFC), polyethylene (PE) and poly(vinyl chloride) (PVC)) (Schützner et al., Anal. Chem. 64 (1992) 1991-) has also been investigated and very similar surface characteristics were found. In contrast to fused silica, the zeta potentials, and thereby also the electro osmotic flow (EOF), obtained using these polymeric materials are influenced only to a small extent by addition of organic solvents, like ethanol, acetonitril or dimethyl sulphoxide, in the electrolyte. Polymeric materials have not been studied in more detail to date, maybe due to the difficulty to make and/or buy uniform hollow fibers with small i.d. (50–60 $\mu$m) as well as the disadvantage of low UV transparency of these materials.

Polypropylene hollow fibers have recently become an interesting alternative to fused silica capillaries for capillary electrophoresis due to their transparency in the visible and near UV region (Nielen et al., J. High Resolut. 16 (1993) 62-). This property also makes polypropylene hollow fibres well-fitted for fluorescence detection systems (Nielen et al., J. Chromatog. 608 (1992) 85-). A potential problem of neat polypropylene or other hydrophobic polymeric materials, such as polyvinyl chloride (PVC), PFC, PE etc, is their hydrophobicity that results in low surface wetability by aqueous solutions. This can lead to severe hydrophobic surface-analyte interactions making it impossible to analyze compounds like proteins on untreated hollow fibers made of this type of material. A hydrophilic surface coating should therefore be of advantage in order to minimize adsorption. Poppe et al (Busch et al., J. Chromatog. 695 (1995) 287-) recently reported on the use of crosslinked hydroxypropyl cellulose (HPCc) to modify the inner surface of a polypropylene hollow fiber. A separation of basic proteins on HPCc treated fused silica capillaries and polypropylene hollow fibers, respectively, resulted in comparable relative standard deviations (RSD) of the migration times and theoretical plate numbers. Covalent bonding of polyacrylamide to polypropylene hollow fibers has also been reported (Liu et al., J. Microbiol. Sep. 15 (1993) 245-; and Liu et al,. J. Microbiol. Sep. 6 (1994) 581-). It has been shown in micellar electrokinetic capillary chromatography (MECC) that a surfactant like sodium dodecyl sulphate (SDS) adsorbed to a polypropylene surface resulted in a high and pH independent electro osmotic flow (Fridström et al., Chromatographia 41 (1995) 295-).

The ideal surface for protein analysis in capillary electrophoresis is a surface which is stable over a wide pH range and which in particular have a high hydrophilicity minimizing adsorption. Dextran polymers have in general been found to possess these properties. Dextran is a hydrophilic polymer known to have low protein adsorption, and is capable of being derivatized with hydrophobic functional groups. It has been shown that membranes coated by dextran resulted in decreased protein adsorption (Henis et al, U.S. Pat. No. 4,794,002). Hjertén et al (Electrophoresis 14 (1993) 390-) found that crosslinked allyldextran on a fused silica surface resisted washing with sodium dodecyl sulphate in alkaline solutions. Mechref et al (Electrophoresis 14 (1993) 390-) have reported high pH-stability of dextran-polyethylene glycol crosslinked surfaces on fused silica. If the dextran has non-polar substituents that can be attracted by physical adsorption to the propylene surface it should be possible to utilize this physical attraction to give a stable surface without the requirement to chemically bind the dextran to the wall or by internal immobilization.

The use of various hydrocarbyl (alkyl, alkenyl and/or phenyl) substituted polyhydroxy polymers for preparing and/or attaching gel layers or hydrophilic coats to plastic surfaces has also been described (Allmér WO 9529203; Henis et al (U.S. Pat. No. 4,794,002 and US 5,139,881); Varady (U.S. Pat. No. 5,030,352); Ericsson et al (SE 9600612-7), and Söderberg U.S. Pat. No. 4,094,832).

OBJECTIONS OF THE INVENTION

The primary objective of the invention is to provide new capillary electrophoresis supports combining the mechanical and chemical stability of fused silica capillaries with low electro osmotic flow, weak or no surface interaction with electrophoresed substances, transparency, etc.

THE INVENTION

The results presented below in the experimental part show for the first time that this objective can be achieved for capillaries made up of plastics in case their inner walls are coated with a hydrophilic polymer exhibiting hydrophobic groups. Accordingly, the invention is a method for capillary electrophoresis utilizing a capillary tube made up of a hydrophobic plastics. The method is characterized in that the inner surface of said capillary is coated with a hydrophilic polymer comprising a polyhydroxy polymer exhibiting groups

—B—R, where R is a hydrocarbyl group and B is a bridge linking R to the polyhydroxy polymer via the free valence indicated, preferably by replacing a hydrogen in a hydroxy group of the polyhydroxy polymer.

By capillary is meant a hollow tube which is capable of retaining by itself the aqueous solution used for electrophoresis. Normally this means tube diameters of 5–500 $\mu$m, the exact limits being dependent on surface characteristics and constituents present in the solution. The length of CE capillaries may vary within wide limits but in most cases they should be within the range 5–100 cm.

The plastics of the capillaries of the invention is a hydrophobic polymer exhibiting a plurality of hydrocarbyl repeating units. It is preferentially a polypropylene, polyethylene, polyvinyl chloride, polystyrene or a polymer of a fluorinated hydrocarbon etc, or a copolymer in which propylene, ethylene, styrene or vinyl chloride fluorinated alkene constitutes one type of monomeric unit. Among fluorinated plastics (PFC) may be mentioned Hostaflon (Hoechst AG, Germany).

The hydrophilic polymer is soluble in water, i.e. in most cases its water solubility is greater than 0.01 mg/ml and may in some cases also be above 10 mg/ml.

The polyhydroxy polymer may be fully synthetic or semi-synthetic. It may also be a native biopolymer that if necessary has been modified/derivatized (semi-native bioplymer). Normally the mean molecular weight of the unsubstituted polymer should be within 1,000–10,000,000 Da, in particular 10,000–1,000,000 Da. Basic polymer skeletons may have been derivatized, for instance to provide the appropriate solubility characteristics. Illustrative examples of synthetic polymers are polyvinyl alcohols, poly (hydroxyalkyl acrylates) and corresponding methacrylates, poly(vinyl hydroxy alkyl ethers) etc. Illustrative examples of useful biopolymers are polysaccharides, for instance dextran and cellulose including derivatives thereof. In order not to fully suppress but rather to control the electro endosmotic flow, the polyhydroxy polymer may have been derivatized to contain anion and/or cation exchanging groups, in particular amino groups (primary, secondary, tertiary or quaternary ammonium groups) or carboxy, sulphonic acid or phosphonic acid groups. Ion exchanging groups may be present either in the bridge B or as groups physically separated from the group —B—R.

The hydrocarbyl group R is normally a group that only contains carbon atoms and hydrogen atoms. This, however, does not exclude groups containing both hydrophilic and hydrophobic structures as long as the hydrophobic character of the group allows for adsorption to a hydrophobic plastic surface. The hydrocarbyl group R is preferentially selected from cyclic, straight or branched alkyl, alkenyl, alkynyl, alkylaryl, arylalkyl, and single phenyl and naphthyl, and should contain at least 3, often 5 or more, carbon atoms. In order not to impose water-insolubility onto the substituted polyhydroxy polymer the hydrocarbyl group should not contain more than 10 carbon atoms, or in the alternative the substitution degree may be lowered. Common hydrocarbyl groups are substituted and unsubstituted forms of allyl, propyl, propenyl, 1-methylallyl, butyl, pentyl, benzyl, styryl, phenyl, tolyl, xylyl, mesityl etc. The exemplified specific and generic hydrocarbyl groups given in this paragraph may be substituted as long as their pronounced hydrophobic character is maintained.

The bridge B is a direct link to a hydroxy group of the polyhydroxy polymer or an organic structure that preferentially is hydrophilic in the sense that the ratio between the sum of oxygen/nitrogen atoms and carbon atoms is greater than 1/4, preferably greater than 1/3. The oxygen/nitrogen atoms possibly linking the terminals of the bridge B to the polyhydroxy polymer and hydrocarbyl group R, respectively, then being included in the sum of nitrogen and oxygen atoms. This means that the preferred bridge B is a hydrocarbon chain that may be straight, branched or cyclic, and optionally also broken with one or more oxygen or nitrogen atoms and/or substituted with one or more hydroxy groups. For stability reason at most one oxygen atom should be bound to one and the same carbon atom. This also means that the preferred bridge B only contains hydrolytically stable structures such as hydroxy, amino, ether, carboxy and hydrocarbon structures. This in turn means that also groups containing other hydrophilic atoms such as sulphur may equally well also be included, for instance sulphone amide and thioether groups. The length of the bridge is normally not more than 12 atoms. Examples of less preferred structures in the bridge are ester groupings (—CO—O— or —O—CO—) and groups of similar hydrolytic stability.

The degree of substitution of the polyhydroxy polymer may vary, but the thumb of rule being that it is high enough to provide for adsorption to the hydrophobic plastic capillary used and low enough to provide for efficient water solubility and low physical adsorption of the substances to be electrophoresed. In figures this means that normally there is below one —B—R group per monomeric group of the polymer, such as below 0.5 or below 0,1–B—R group per monomeric unit of the polymer. An illustrative range is 0.01–1 with preference for 0.1–0.4 —B—R group per monomeric unit. These figures are particularly well adapted to polysaccharides, e.g. dextrans.

For polyhydroxy polymers having a low degree of substitution and/or being substituted with small hydrocarbyl groups, the adsorbed hydrophilic polymer may be crosslinked after adsorption in order stabilize the hydrophilized surface. Crosslinking may be achieved by selecting unsaturated hydrocarbyl groups, like allyl, that may undergo polymerisation after adsorption. See the experimental part. Crosslinking may also be accomplished with bifunctional nucleophilic reagents that creates bridges between hydroxy group of the basic polyhydroxy polymer. Examples of suitable cross-linking reagents are epihalo hydrin, bisepoxides and other similar reagents that also give rise to the most preferred bridges B: —CH$_2$CHOHCH$_2$—O—, —CH$_2$CHOHCH$_2$—O—CH$_2$CHOHCH$_2$—O—, —CH$_2$CHOHCH$_2$CH$_2$CHOHCH$_2$—O— etc.

The coating procedure is carried out by contacting the capillary inner surface with an aqueous solution containing the hydrophilic polymer under a sufficient time for adsorption. Contact can be accomplished either by dipping the capillary into the solution or by forcing the solution to flow through. Temperatures, contact times and pH conditions depend on the hydrophilic polymer, the characteristics of the plastics etc. Normally the temperature should be within the range 20–90° C., the pH within 2–8, with preference for 4–10, and the contact time within 1 min to 48 h although often 1–60 min will be sufficient. Pretreatment steps for cleaning the plastic surface or increase its wetability may also be included. See the experimental part.

The conditions for the electrophoresis is the same as usually applied to capillary electrophoresis, for instance 50–500 V/cm. The inventive method of electrophoresis can be applied to resolutions of mixtures of various nucleic acids, including RNA, DNA, fragments thereof, synthetic oligonucleotides; proteins and polypeptides; and low molecular weight charged compounds, such as carboxylic acids and amines.

The best mode of the invention as per the priority date is as indicated above and also illustrated in the experimental part.

Experimental Part

Chemicals

Lysozyme, cytochrome c and naproxen were from Sigma (St. Louis, Mo., USA). Sodium dihydrogen phosphate, phosphoric acid and disodium tetraborate-10-hydrate were from Merck (Darmstadt, Germany). Ammonium persulphate and warfarin were from Aldrich (Gillingham, Dorset, England). TRIS, tris(hydroxymethyl)amino methane, and TEMED, N,N,N', N'-tetramethylenediamine, were purchased from Bio-Rad Laboratories (Richmond, Calif., USA).

Allyldextran (150,000 and 2×10$^6$ Da) with 1:4 (allyl:glucose) substitution, and phenyldextran (40,000 and 500,000) with 1:5 (phenyl:glucose)substitution were synthesized by reacting dextran with the appropriate Mw with allyl glycidyl ether and phenyl glycidyl ether, respectively, under alkaline condition in the presence of NaBH$_4$.

Instrumentation

All experiments were carried out on a Dionex Model CES-1, capillary electrophoresis system (Dionex, Sunnyvale, Calif., USA) without termostating. Data were collected with a Model SP 4290 integrator (Spectra Physics, San Jose, Calif., USA) and transferred via RS 232 to a computer. Data files were evaluated with Igor, Graphing and Data Analysis (Wave Metrics Inc., Lake Oswego, Oreg., USA) on a Macintosh computer. Detection was done with on column absorbance at 280 and 240 nm.

Pretreatment of Polypropylene and Polyethylene Films for Contact Angle Measurements The polymeric films were washed over night in acetone. Before the adsorption of phenyldextran the films were dried in air. The polymeric films were left over night in a water solution of 2% (w/v) phenyl dextran or allyl dextran. This incubation was performed at 60° C. after which the films were rinsed in water and ultrasonicated during 10 minutes in water. Contact angle measurements were performed on air dried polypropylene and polyethylene films. The results are presented in FIG. 1 (average of five replicates).

General Dynamic Column Coating Procedure

The columns 65 μm i.d. and 120 cm length, were prewashed with 3 ml acetone. A water solution of 1% (w/v) dextran substituted with allyl glycidyl or phenyl glycidyl groups was purged by $N_2(g)$ at a pressure of 80 psi through the column for one hour. The columns were then left during night filled with the dextran solution. The middle part (50–60 cm) of each column was the used for the analysis in capillary electrophoresis. A washing and equilibration step (3×10 min) was performed with the running electrolyte in the CE system before testing of the column.

Coating and Crosslinking of Allyldextran to the Polypropylene Surface (1) A degassed solution of ammonium persulphate (10% (w/v) was pushed through the column with $N_2(g)$ at a pressure of 80 psi column (the column had been prewashed with 3 ml acetone). Termostating was performed using a water bath at 80° C., during two hours. (2) The reaction temperature was lowered to 50° C. Allyl dextran 2% (w/v), 150,000 or $2\times10^6$ Da, and ammonium persulphate 5% (w/v) was dissolved in 50 mM TRIS at pH 8.0 and degassed before addition of TEMED 1.5% (v/v). During 8 hours, the reaction solution was kept continuously flowing through the column with a nitrogen gas pressure of 80 psi.

Results and Discussions

Contact Angle Measurements

Contact angle measurements were performed on flat polymeric films of polymeric materials (polyethylene and polypropylene) modified by adsorption of different kinds of dextrans in order to evaluate the wetability effects caused by the modification. The variance in contact angle measurements were large and it was therefore appropriate to evaluate relative measurements.

In FIGS. 1A and 1B, the advancing and receding contact angle, respective, are plotted against the substitution degree of the used polyhydroxy polymer. It was found that for phenyl dextran there was a dramatic influence on the receding contact angle for both polypropylene and polyethylene surfaces (FIG. 1B). The advancing contact angle on the other hand was less effected (FIG. 1A), i.e. the wetability is dependent on the contact time. The results illustrates that surfaces increase in hydrophilicity by coating with the polyhydroxy polymers used.

Electrophoretic Conditions

When using polypropylene columns in capillary electrophoresis (CE) it should be considered that the dissipation of heat is much lower for a plastic column than for fused silica columns. The CE instrument used in this study had no facilities for termostating the column. To avoid a destructive temperature gradient, a rather low electric field, around 200 V/cm, was used for all measurements. The pH of the system was selected to 2.7 since at this pH-value the tested proteins (lysozyme and cytochrome c) are fully charged which means a shortening of the migration times.

Coating Procedures

The effect of pretreatment was done on polypropylene surfaces and coating with phenyldextran of Mw 40 kDa. The choice of prewashing solvent (methylene chloride, tetrahydrofurane and acetone) was found to have measurable effects on the coating. The best effects were obtained for acetone. For methylene chloride and tetrahydrofurane the adsorption of the polyhydroxy polymer to the surface was in fact decreased.

Columns that were treated with a solution of 1% phenyl dextran showed reproducible migration times while lower concentrations, i.e. 0.5% (w/v), gave non-reproducible data. Surface modifications with even higher concentrations were also tested, but there were no improvements for concentrations of 3% and 5% solutions no improvements in number of plates (N) or in migration time stability compared to the results presented in Table 1. Further studies were therefore performed on columns coated with 15% (w/v) phenyl dextran solutions.

Efficiencies and Migration Times in Electrophoresis

To study the surface characteristics of the coated column, efficiencies and migration times were investigated, see Table 1. In the literature, it is common to use cytochrome c and lysozyme in protein standard mixtures for testing surface modifications in CE on both fused silica columns (Gilges et al., Anal. Chem. 66 (1994) 2038-; Huang et al., J. Microbiol. Sep. 5 (1993) 199-; Schmalzing et al., J. Chromatog. A. 652 (1993) 149-; and Gilges et al., J. High Resolut. 15 (1992) 452-) and polypropylene hollow fibers (Liu et al., J. Microcol. Sep. 15 (1993) 245-; Busch et al., J. Chromatog 695 (1995) 287-; and Liu et al., J. Microcol. Sep. 6 (1994) 581-). The relative standard deviation (RSD) of the migration times for these proteins were 0.9% for cytochrome c and 1.4% for lysozyme when using 40 kDa phenyldextran, while 500 kDa phenyl dextran showed higher RSD values, i.e. 1.9% and 2.7% for cytochrome c and lysozyme, respectively. On the other hand, the efficiencies were higher on the column modified by the 500 kDa phenyldextran. It was also noted that the α values were comparable for the two coatings which means that the selectivity was not affected by the size of the phenyldextran used.

Effects of Washing Steps Between Electrophoretic Experiments

Real samples often contain analytes that remain strongly bound to a column which may alter characteristics of the column. It is then important that the column surfaces can be washed under harsh conditions, e.g. with solutions of sodium hydroxide. It was found that separation of the protein standards could be accomplished after washing with 0.1 M NaOH for 15 minutes of the polypropylene column modified with phenyl dextran. This indicates that the coating is not removed under these conditions. See FIG. 2. Surprisingly, the efficiency was increased while the migration times of the two peaks were increased and the peak heights were decreased. The latter effect was most pronounced for cytochrome c. Since cytochrome c always gave a lower efficiency cytochrome c was found to be more sensitive to adsorption effects than lysozyme. The efficiency was not improved by decreasing the amount of cytochrome c (i.e. 0.1 mg/ml instead of 1 mg/ml) which excludes overloading. Because of the uncharged character of the column surface, ionic interactions can not be the main reason for the broadening of the cytochrome c peak. A more plausible explanation could be specific interactions with the phenyl groups of the coating or that cytochrome c still can interact with the polypropylene surface because of an incompletely coated surface.

Experiments with Allyl Dextran

In order to attach a crosslinked polyhydroxy polymer to a polypropylene surface, a published method for free radical grafting/crosslinking of acrylamide (Liu et al., J. Microcol. Sep. 15 (1993) 245-) was slightly modified and applied to allyldextran. The so obtained column material enabled electrophoretic separation of our protein standard sample. The separation, however, was not as good as in columns coated with phenyl dextran (see FIGS. 3A and 3B) which indicates that the surface coverage for allyldextran was incomplete.

Migration Behaviour of Negatively Charged Organic Carboxylic Acids

In this part of our study the acids were warfarin and naproxen. Untreated and phenyldextran modified polypropylene columns were used under the same conditions except that the polarity of the voltage had to be reversed for the later column since the electro osmotic flow was too low to move negatively charged solutes toward the detector at the anode. The electro osmotic flow at pH 9.2 on the phenyldextran modified polypropylene column as measured to $1.2 \times 10^{-4}$ cm$^2$V$^{-1}$. As a comparison, the electro osmotic flow on an untreated polypropylene surface was $4 \times 10^{-4}$ cm$^2$V$^{-1}$. The migration times was reproducible on both the modified and the untreated surface, 0.4% (n=5) and 0.8% (n=5), respectively. The modified surface also gave an improved efficiency for the warfarin and naproxen peaks from 40,000 to 130,000 theoretical plates on the 45 cm column lengths. The RSD for the efficiencies were 4–6% on both the naked polypropylene surface and the phenyldextran coated surface.

Conclusion

The results of this study show that it is possible to accomplish stable plastic columns for capillary electrophoresis by simple adsorption of hydrophilic polymers exhibiting hydrophobic functional groups. Using tailor-made polymers that can provide both wetability and crosslinking it should be possible to get even higher stability through immobilization of this type of hydrophilic polymers.

FIGURE CAPTIONS

FIG. 1. Advancing (A) and receding (B) contact angles as a function of degree of phenyl substitution (phenyl:glucose) of dextran on polypropylene and polyethylene films.

Figure 2:
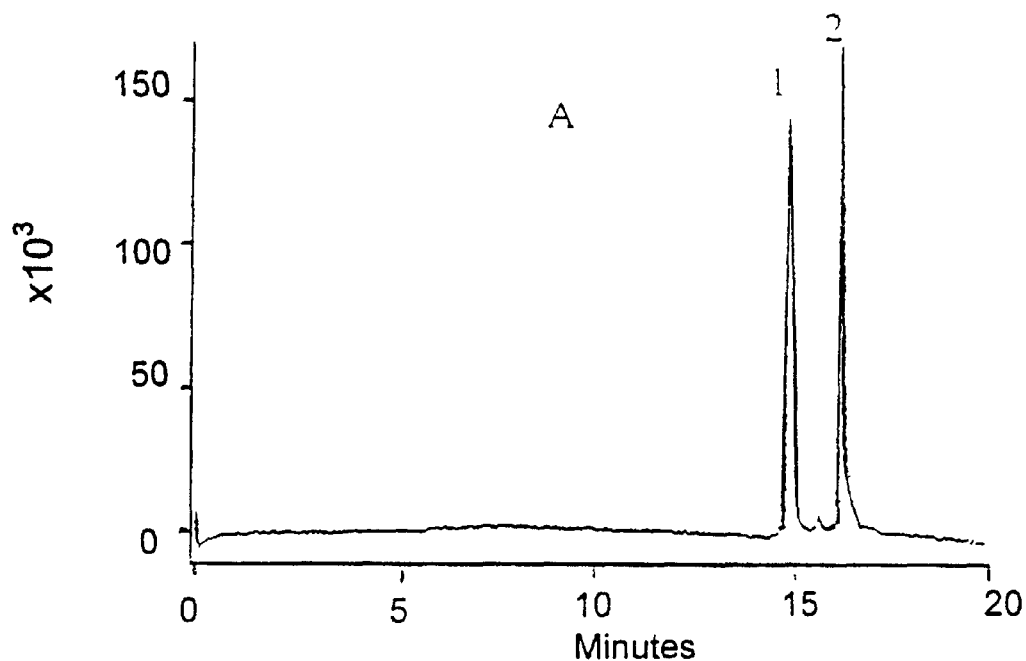
Figure 2:
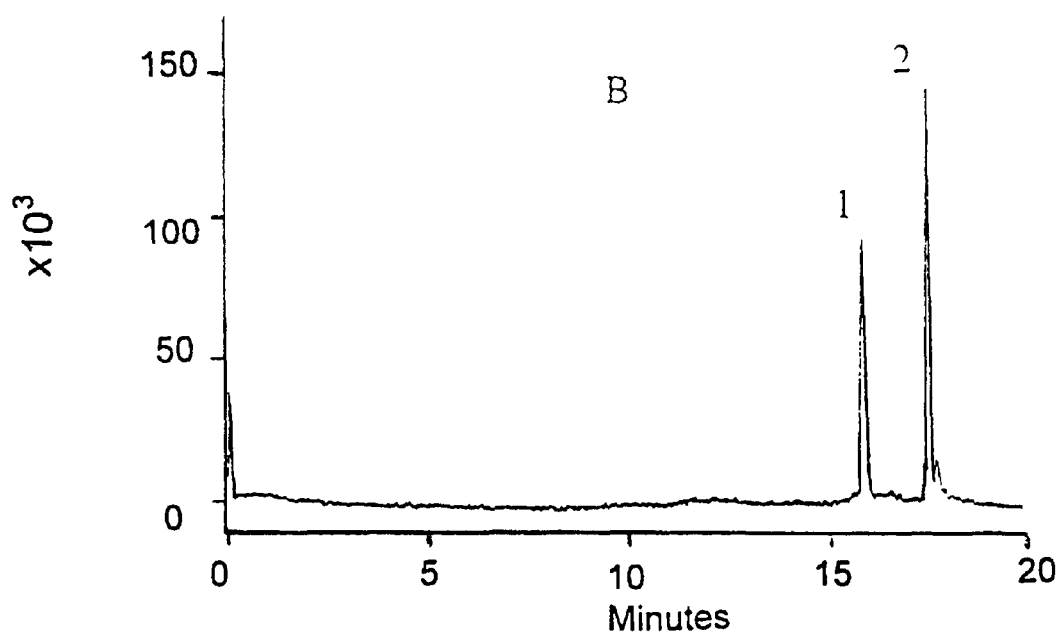

FIG. 2. Surface stability of a polypropylene column modified with 500 kDa phenyldextran for the analysis of protein standards before (A) and after (B) washing with 0.1 M NaOH solution. Peak identification: cytochrome c(1) and lysozyme (2). Conditions: 50 cm×65 μm (i.d.) column with 45 cm to detector; 50 mM phosphate buffer at pH 2.7; +9 kV applied voltage; 280 nm (au 0.01) UV detection.

Figure 3:
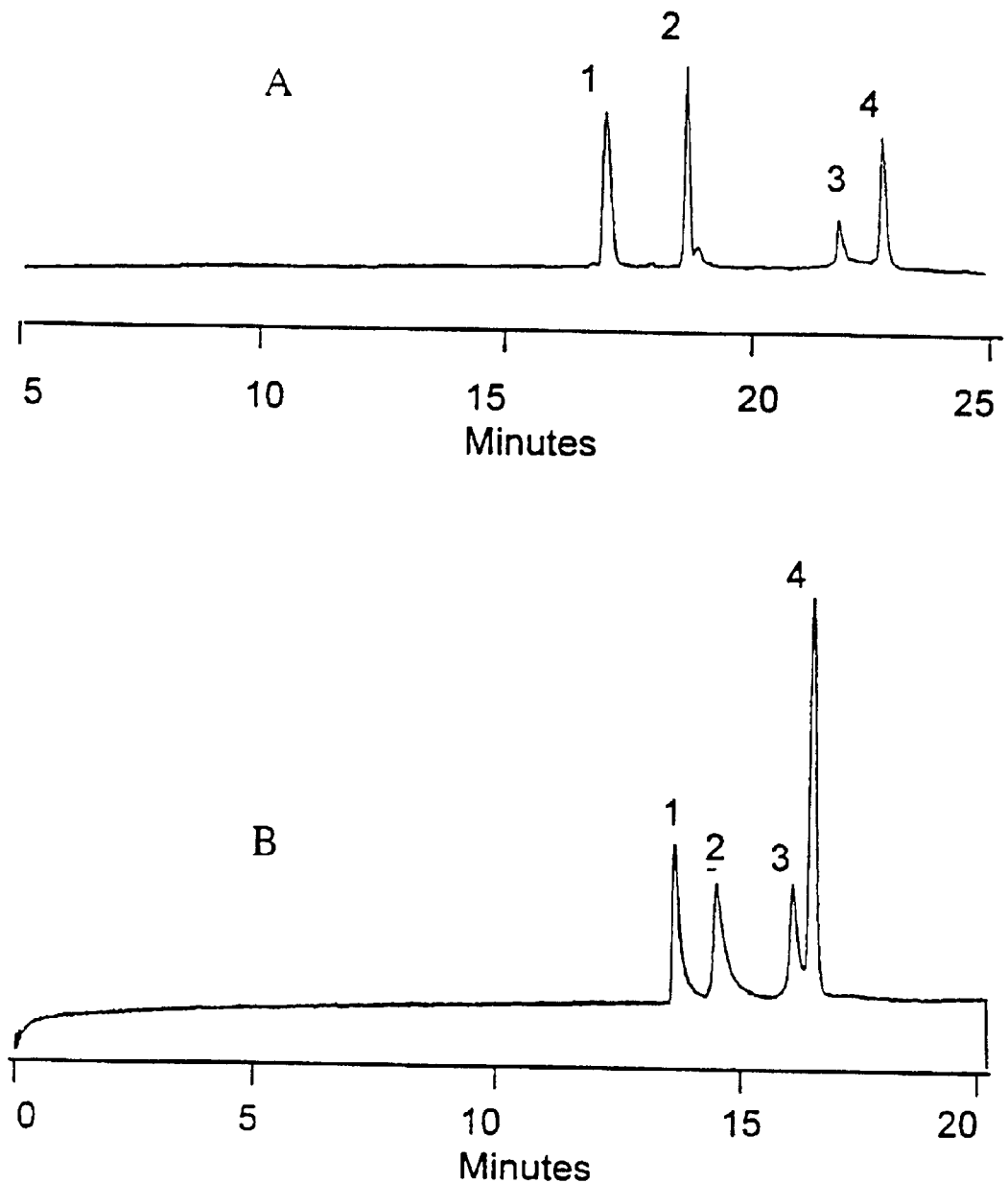

FIG. 3. Protein separation on adsorbed phenyldex.ran (A) and immobilized allyldextran (B) modified polypropylene surfaces. Peak identification: cytochrome c (1), lysozyme (2) ribonuclease A (3) and chymotrypsinogen (4). Condition: 50 cm×65 μm (i.d.) column with 55 cm to detector; 50 mM phosphate buffer at pH 2.7; +12 kV applied voltage; 280 nm (au 0.01) UV detection.

Figure 4:
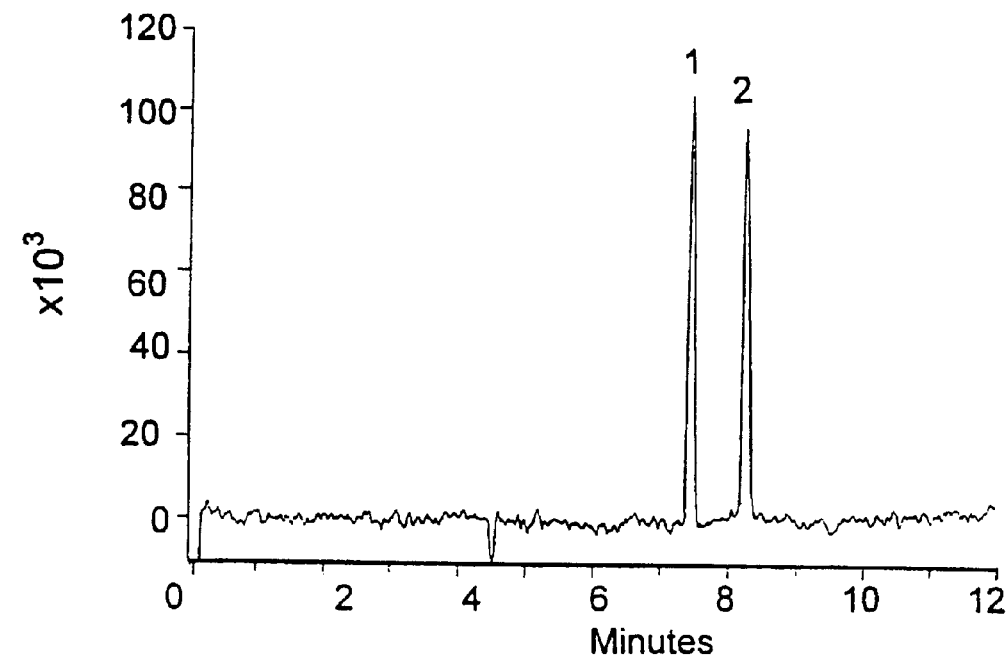
Figure 4:
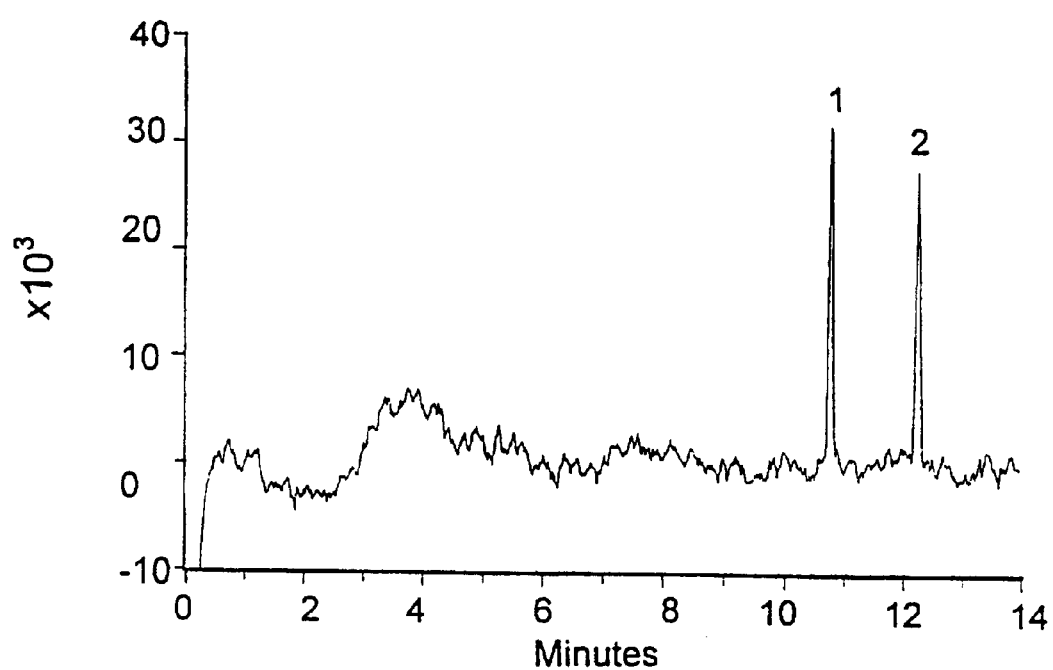

FIG. 4. Migration of warfarin (1) and naproxen (2) on untreated (A) and phenyldextran (B) modified polypropylene surfaces. Conditions: 50 cm×65 μm (i.d.) column with 45 cm to detector; 17 mM borate buffer at pH 9.2; +15 kV (A) and −15 kV (B) applied voltage; 240 nm au 0.01 (A) and au 0.02 (B) UV detection.

TABLE I

Performance of Phenyldextran Coated Polypropylene Surfaces

| Protein | Phenyl-dextran (Mw) | Migration time (Mean) | n | RSD (%) | Theoretical plate number (N) | RSD (%) |
|---|---|---|---|---|---|---|
| Cyt. c[a] | 40 000 | 16.24 | 22 | 0.9 | 76 000 | 5.4 |
| Lys.[b] | 40 000 | 17.35 | 22 | 1.4 | 222 000 | 7.3 |
| Cyt. c | 500 000 | 17.23 | 21 | 1.9 | 91 500 | 12.5 |
| Lys. | 500 000 | 18.56 | 21 | 2.7 | 260 000 | 11.7 |

Conditions the same as in FIG. 2.
[a]Cytochrome c
[b]Lysozyme

What is claimed is:

1. A method of capillary electrophoresis comprising the steps of introducing a sample into a capillary tube and subjecting said capillary tube and said sample to an electric field for electrophoresis, wherein said capillary tube is made up of hydrophobic plastics and comprises an inner surface coated with a hydrophilic polymer comprising a polyhydroxy polymer exhibiting groups

—B—R wherein R is a saturated or unsaturated hydrocarbyl and B is a hydrocarbon chain that may be straight, branched or cyclic and binds to the polyhydroxy polymer.

2. The method of claim 1, wherein the substitution degree of —B—R groups is within the range 0.01–1 —B—R group per monomeric unit of the polyhydroxy polymer.

3. The method according to claim 1, wherein R is an allyl.

4. The method according to claim 1, wherein R is a phenyl.

5. The method according to claim 1, wherein R is a benzyl.

6. The method according to claim 1, wherein the hydrophilic polymer also exhibits ion exchange groups.

7. The method according to claim 1 wherein the polyhydroxy polymer is dextran.

8. The method according to claim 1, wherein said hydrocarbon chain in B is broken with one or more oxygen atoms or substituted with one or more hydroxyl groups.

9. The method according to claim 1, wherein R comprises at least three carbon atoms.

10. The method according to claim 1, wherein the capillary has a diameter of between 5 to about 500 micron.

11. The method according to claim 1, wherein the hydrocarbyl containing polyhydroxy polymer is water-soluble.

* * * * *